United States Patent [19]

Toppses et al.

[11] Patent Number: 5,311,863

[45] Date of Patent: May 17, 1994

[54] LASER RESISTANT ENDOTRACHEAL TUBE, TAPE, MATERIAL AND ARTICLE

[75] Inventors: Anthony N. Toppses, Gansevoort; David S. Sheridan, Argyle, both of N.Y.

[73] Assignee: Sheridan Catheter Corp., Argyle, N.Y.

[21] Appl. No.: 897,841

[22] Filed: Jun. 12, 1992

[51] Int. Cl.$^5$ ............................................. A61M 16/00
[52] U.S. Cl. ............................. 128/207.15; 128/207.14
[58] Field of Search ....................... 128/200.26, 207.14, 128/207.15

[56] References Cited

U.S. PATENT DOCUMENTS

| | | | |
|---|---|---|---|
| 4,098,728 | 7/1978 | Rosenblatt | 521/141 |
| 4,632,108 | 12/1986 | Geil | 128/207.14 |
| 4,834,087 | 5/1989 | Coleman et al. | 128/207.14 |
| 5,065,757 | 11/1991 | Dragisic et al. | 128/207.14 |
| 5,103,816 | 4/1992 | Kirschbaum et al. | 128/911 |
| 5,139,019 | 8/1992 | Smith et al. | 128/207.15 |

OTHER PUBLICATIONS

M. Sosis, "On the Development of a New Laser-Resistant Endotracheal Tube", J. Clin, Anesth. 4:87–88, 1992.
J. M. Green et al., "The Resistance to Carbon Dioxide Laser Ignition of a New Endotracheal Tube: Xomed Laser-Shield II", J. Clin. Anesth. 4:89–92, 1992.
Anesthesia Update: "Old Concerns Remain, New Ones Added", Clinical Laser Monthly, vol. 10, No. 1, pp. 6, 11–13, 1992.
M. Sosis et al, "Reflection of $CO_2$ Laser Radiation From Laser-Resistant Endotracheal Tubes", Anesth. Analg. 73: 338–340, 1991.
W. Mathews, "A Method for Determing Depth of Unmarked Endotracheal Tubes Used in Laser Surgery", Anesth. Analg. 70: 340, 1990.
A. DeRichmond, ECRI: "Laser-Resistant Endotracheal Tubes and Wraps", Health Devices 19(4): 109–110, 112–113, 116–139, 1990.
R. Ossoff, "Laser Safety in Otolaryngology–Head and Neck Surgery: Anesth. & Educat. Consid. for Larygeal Surgery", Laryngoscope 99 (8) 1–26, 1989.
V. Patil et al, "A Modified Endotracheal Tube for Laser Microsurgery", Anesthesiology 61 (9): 571, 1979.
Xomed-Treace, Laser-Shield II, "Endotracheal Tube Cuffed (For $Co_2$ and KTP Lasers Only", Product Information and Instructions.
Mallinckrodt Critical Care, "Laser-Flex Disposable, Laser Resistant Tracheal Tube".

Primary Examiner—Edgar S. Burr
Assistant Examiner—Aaron J. Lewis
Attorney, Agent, or Firm—Burns, Doane, Swecker & Mathis

[57] ABSTRACT

A laser resistant endotracheal tube having a laser resistant layer surrounding the tube for at least a portion of the tube length. The laser resistant layer has a plurality of surface irregularities that are spaced from one another in a plurality of directions and which reflectively scatter laser energy. The laser resistant layer can be applied as an adhesive backed tape which has adhesive on only a portion of the width so that when the tape is spirally wrapped around the tube, the adhesive substantially avoids contact with previously wrapped tape. The tube can be provided with an inflatable cuff that is protected from degradation by an adjacent protective collar and the collar and a portion of the laser resistant layer can be covered with a laser resistant collar. The laser resistant layer can be covered by a cut resistant textile. A laser resistant tape, material and article are also disclosed.

25 Claims, 2 Drawing Sheets

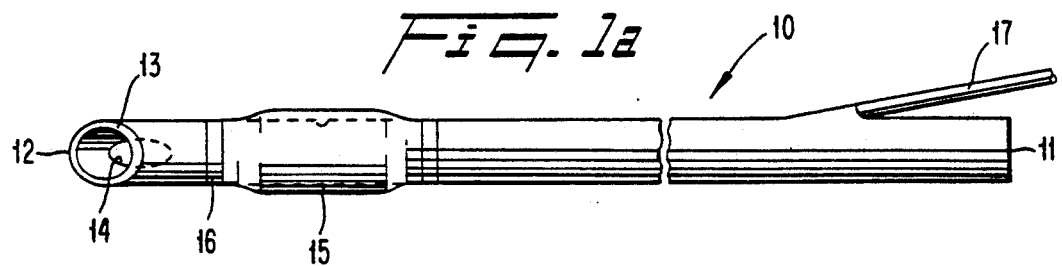
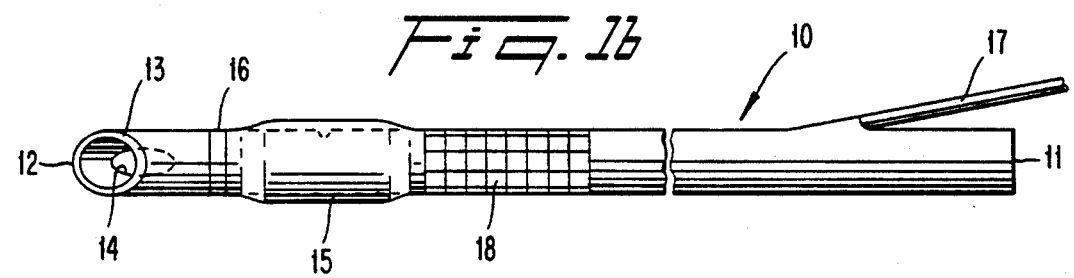
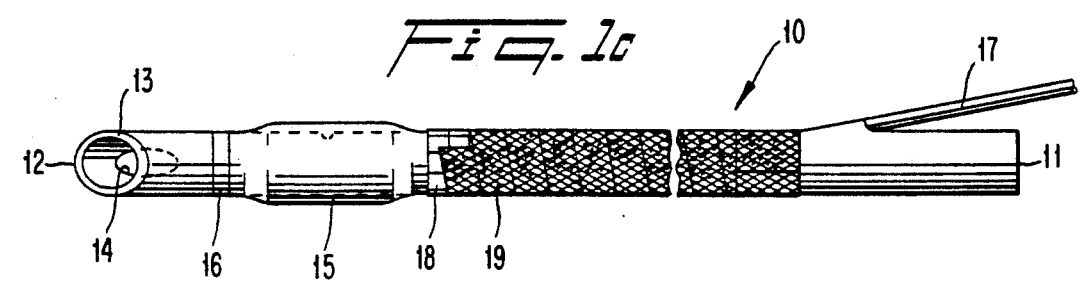
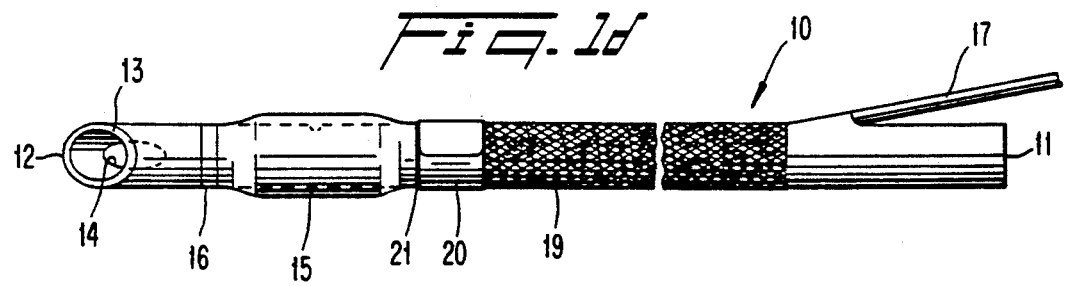
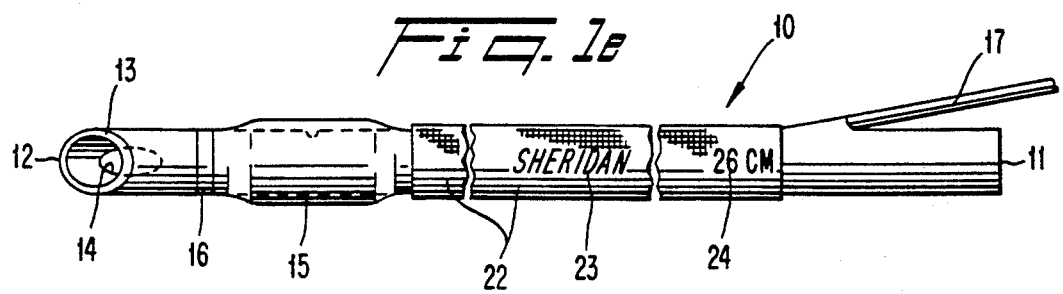

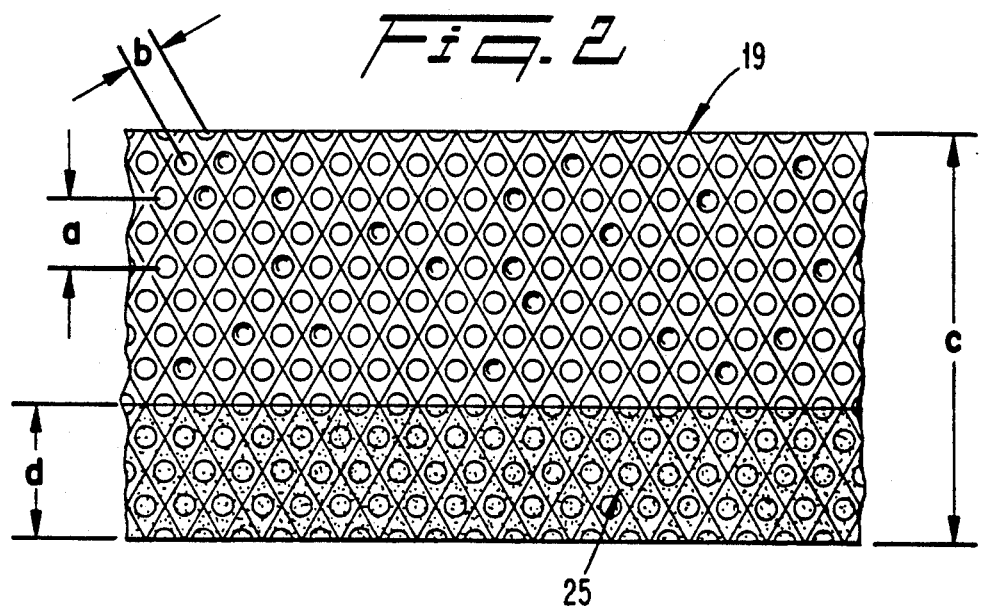
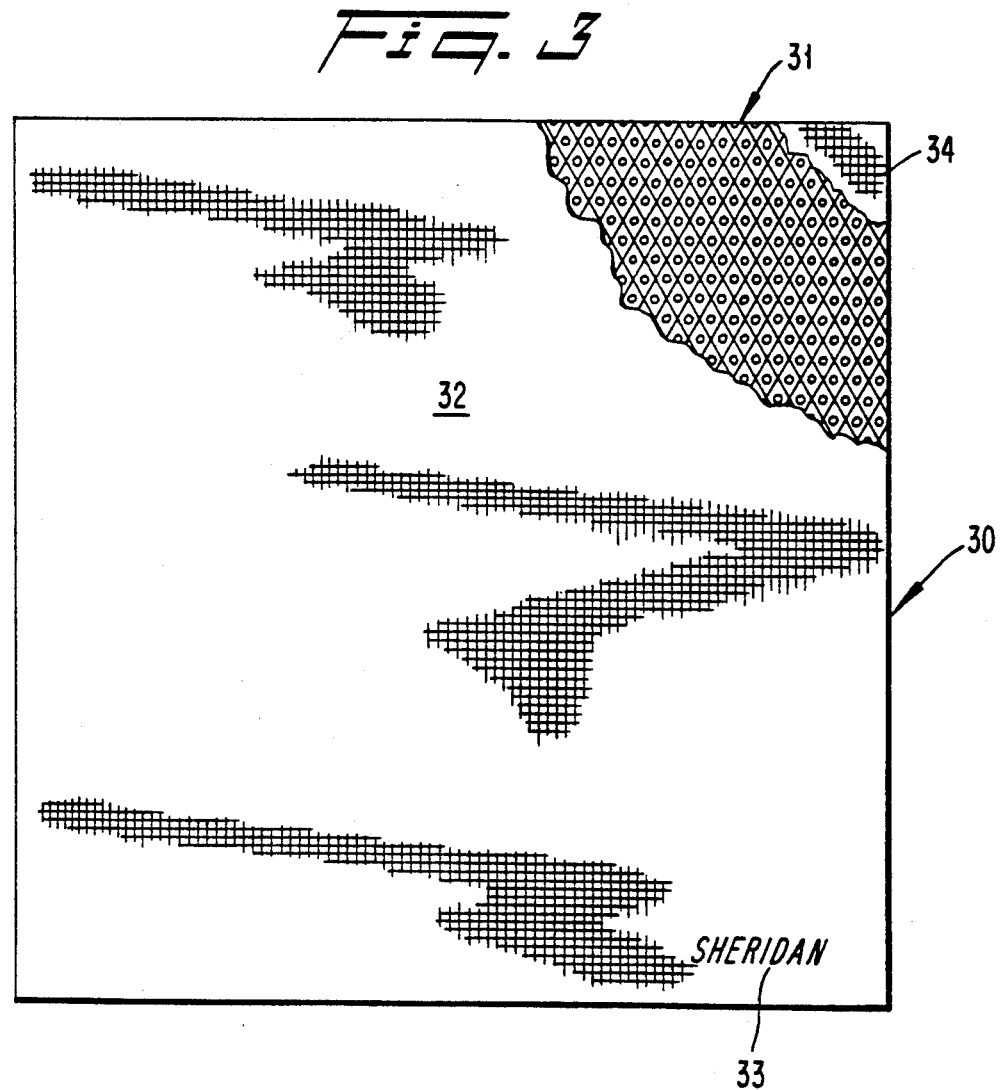

LASER RESISTANT ENDOTRACHEAL TUBE, TAPE, MATERIAL AND ARTICLE

BACKGROUND OF THE INVENTION

1. Field of the Invention

The present invention relates to a laser resistant ventilation device and to laser resistant tape, material and article.

2. Description of the Related Art

Laser radiation has been finding increased use in medicine due to its adjustable power, the potential precision of its use and its hemostatic property. However, inadvertent application of laser energy on non-target areas or inflammable items which are present in the vicinity of laser application can lead to serious injury of the patient. One particular concern is the use of laser radiation in the vicinity of an emplaced endotracheal tube. It has been found that when laser energy is applied to conventional endotracheal tubes, the tubes are thermally degraded and, if the ventilating gas contains a high percentage of oxygen, can result in a "blowtorch" phenomenon with potentially serious adverse consequences to the patient.

In an effort to meet this potential problem, the art has used a variety of protective devices for endotracheal tubes. For instance, the tube has been wrapped with muslin or gauze that has been saturated with saline solution. While this provides a certain level of protection of the endotracheal tube, if the laser energy resides in one location for more than a few seconds, the afforded protection will be lost and the endotracheal tube will be degraded.

Another manner of protecting the endotracheal tube is by wrapping the tube with copper or aluminum foil which is in tape form. Although the metallic foil generally protects the endotracheal tube, the laser energy can reflect off the surface of the foil and cause injury to non-target areas of the patient or to operating room personnel. Additionally, when the endotracheal tube is flexed, the foil can kink and impair ventilation of the patient, particularly if a small diameter tube is used, or can separate from localized areas of the tube, leaving gaps in the protection and exposing relatively sharp edges which can injure the patient upon removal. The metallic foil can also degrade the inflatable cuff and therefore is spaced from the cuff which detracts from the area of laser protection afforded the tube.

A commercially available kit designed to provide laser protection to conventional endotracheal tubes involves a micro-corrugated silver foil that is wrapped around the tube and is in turn enveloped in a hydrophilic sponge comprised of the reaction product of polyvinyl alcohol and formaldehyde. The sponge is described in U.S. Pat. No. 4,098,728.

Another manner of protecting conventional endotracheal tubes is described in U.S. Pat. No. 5,103,816. As set forth therein, the tube is spirally wrapped with a composite of an adhesive layer, foil, a fire retardant fabric and a hydrogel.

Other attempts at laser resistant endotracheal tubes involve the construction of the tube itself. For instance, the so-called Baxter-Norton tube is constructed of an interlocked, flexible, stainless steel, spiral with the distal tip and the ventilator connector brazed thereon. The tube is not airtight and is not provided with an inflatable cuff.

U.S. Pat. No. 4,834,087 and its division, U.S. Pat. No. 5,040,531, describe an endotracheal tube constructed of an airtight flexible tube having a matte outer surface to reduce reflection. However, the matte surface tends to absorb laser energy causing a significant increase in the temperature of the metal which can cause thermal damage to the surrounding tissue.

Other types of endotracheal tubes are constructed of an aluminum and silicone spiral with a silicone covering or a silicone tube covered with a protective aluminum-filled silicone layer. The silicone-containing materials generally do not provide a sufficient level of laser resistance. Furthermore, if they are thermally degraded by laser energy, an ash-like material remains which can be difficult to completely remove from the patient.

A further type of laser resistant endotracheal tube includes a piece of flat aluminum foil that is spirally wrapped around a cuffed tube. The aluminum foil is not adhesive backed, but is maintained in place by the pressure of the spiral wrapping and secured near the proximal end of the tube with tape. The aluminum foil layer is covered with a Teflon overwrap. The absence of adhesive on the foil makes such an endotracheal tube relatively difficult to manufacture and has the potential of unraveling. Additionally, if the Teflon overwrap is impacted with laser energy, it can cause a medical condition known as "plume polymer fever". Furthermore, if the laser energy burns through the Teflon overwrap and impacts the aluminum foil layer, it can reflect and cause injury to the patient or surgeon.

A discussion of various types of endotracheal tubes used in laser surgery and their performance is in "Health Devices", Vol. 19, No. 4, pages 109–139 (April 1990).

An ancillary problem with respect to endotracheal tubes designed to be used in laser surgery is placing the tube in the correct position within the patient. Conventional endotracheal tubes have marks to indicate distance from the distal end. However, dark marks tend to absorb laser energy and are thus omitted from certain tubes designed for use with laser surgery. Additionally, the material of construction of some laser resistant tubes is difficult to mark and marking is likewise omitted. This problem and a technique for measuring the depth of unmarked endotracheal tubes is described in a Letter to the Editor by Dr. Wayne S. Matthews, Jr. in Anesth. Analg., Vol. 70, page 340 (1990).

Despite the numerous developments that have been made in the art, significant drawbacks remain and the art has continued its search for an effective laser resistant endotracheal tube and material. Improved techniques for protecting articles and individuals from laser energy are also being sought in the art.

OBJECTS AND SUMMARY OF THE INVENTION

It is accordingly one object of the present invention to provide an improved laser resistant endotracheal tube.

It is a more specific object to provide an endotracheal tube which has laser protection over a greater portion of the tube.

It is another object of the invention to provide an endotracheal tube which, has a metallic layer that causes scattered reflection of laser energy.

It is a further object of the present invention to provide a laser resistant endotracheal tube which can be easily placed into position within a patient.

It is a further object of the present invention to provide a laser resistant endotracheal tube which does not increase the tube's tendency to kink and bends without compromising laser resistance.

It is a still further object of the present invention to provide a laser resistant endotracheal tube which has an outer textile layer that resists cutting by sharp objects.

It is a still further object of the present invention to provide a laser resistant endotracheal tube which contains identification or instructional markings on an outer textile surface which markings do not substantially adversely affect the laser resistance of the endotracheal tube.

It is a yet further object of the present invention to provide a laser resistant tape that can be wrapped around objects to afford laser protection.

It is a yet further object of the present invention to provide a laser resistant material which can be used in those areas where lasers are being used.

It is an additional object of the present invention to provide an article having laser resistance and flexibility.

Accordingly, in one embodiment, the present invention provides a laser resistant endotracheal tube which comprises:

a) a tube capable of providing gas to a patient, said tube having a distal end for insertion in the patient and a proximal end for connection with a respirating device; and b) a laser resistant layer surrounding the tube along at least a portion of the length of the tube between the distal end and the proximal end, said laser resistant layer comprising a reflective material having a plurality of surface irregularities which are spaced from one another in a plurality of directions and which reflectively scatter laser energy.

In another embodiment, the present invention provides a laser resistant tape comprising a flexible metallic tape with a reflective surface and having a plurality of surface irregularities which are spaced from one another in a plurality of directions and which reflectively scatter laser energy.

In a further embodiment, the present invention provides a laser resistant material comprising a laminate of a laser resistant layer composed of a reflective material having a plurality of surface irregularities which are spaced from one another in a plurality of directions and which reflectively scatter laser energy and at least one additional layer.

In a still further embodiment, the present invention provides a laser-resistant article comprising an article and a laser resistant layer at least partly covering the article, the laser resistant layer being comprised of a plurality of sections of a laser resistant material, at least some of the sections having portions that contact and are adhered to the article and other portions which overlap other sections of the laser resistant material and are free to move in the portions of overlap so that upon flexing of the article, the sections of laser resistant material substantially avoid structural attrition and maintain laser protection.

BRIEF DESCRIPTION OF THE DRAWINGS

FIGS. 1(a) to (e) are side views of an illustrative laser resistant endotracheal tube of the present invention showing the steps of construction with the completed tube depicted in FIG. 1(e).

FIG. 2 is an enlarged side view of an illustrative laser resistant tape of the present invention.

FIG. 3 is a plan view of an illustrative laser resistant material with a partial cutaway to reveal an additional layer.

DESCRIPTION OF THE PREFERRED EMBODIMENTS

One aspect of the present invention relates to a laser resistant endotracheal tube. As may be seen from FIGS. 1(a)–(e), the laser resistant endotracheal tube is prepared from an endotracheal tube of standard construction that is generally indicated at 10. The tube has a proximal end 11 which typically contains a connector (not shown) for connection to a ventilating device (not shown) and a distal end 12 for insertion into a patient. The length of the tube depends on the intended patient (e.g., adult, child, or infant). In general, adult endotracheal tubes have a length from the distal end to the proximal end of from about 30 to about 38 centimeters, preferably from about 32 to about 36 centimeters and most preferably from about 33 to about 35 centimeters with an external diameter ranging from about 6 to about 15 millimeters. The tube may be constructed of a conventional flexible material, such as polyvinyl chloride, silicone, red rubber, latex or other elastomeric materials with red rubber being preferred. The tube is usually preformed into an arcuate shape that is suitable for insertion into a patient as is known in the art.

The distal end of the endotracheal tube typically has a bevelled end 13 and can contain a Murphy eye 14. The tube is usually provided with an inflatable cuff 15 which is attached to the tube by attachment means 16 which may be any suitable adhesive or tape. If appropriate, the overall cuff structure is provided with a layer (not shown) to attain a smooth surface. Such a layer may be applied by dipping the tube in a latex emulsion or other techniques known to those knowledgeable in the art.

The inflatable cuff 15 is typically constructed of a latex material, especially for red-rubber endotracheal tubes, but other materials capable of being formed into an inflatable cuff, such as silicone, may also be used. The cuff can be inflated with air, an inert gas, or preferably water or a saline solution and is preferably constructed so that fluid under pressure, for example from about 0.25 to about 8 p.s.i.g., can be used to inflate the cuff. A latex cuff is preferred since it is generally superior in cut resistance and can be inflated at higher pressures within the stated range whereby deflating the cuff ca be rapidly achieved.

The fluid used to inflate the cuff is provided through tube 17. Tube 17 is usually incorporated within the wall of tube 10 so that a smooth surface is presented, but may also extend along the surface of tube 10. Tube 17 is typically connected to a bubble chamber (not shown) which indicates the inflation status of the cuff and contains a connector (not shown) for connection to a pressurized source of the appropriate inflating fluid.

Although a single inflatable cuff has been illustrated, it should be clear to those of ordinary skill in the art that multiple cuffs with multiple inflation tubes can likewise be used as disclosed in aforementioned U.S. Pat. No. 4,834,087, the contents of which are incorporated by reference.

As shown in FIG. 1(b), a protective collar 18 is located adjacent to inflatable cuff 15. The collar is constructed of an impermeable tear and puncture resistant material which is wrapped around the tube 10. The protective collar also inhibits metal oxide degradation of the cuff which has been encountered in conventional tubes using latex cuffs and metallic foil for laser protection. Although there is no limitation on the longitudinal extent of the protective collar (i.e., from the proximal end of the cuff toward the proximal end of tube 10), it typically extends from the cuff for from about 5 to about 50 millimeters, preferably from about 20 to about 30 millimeters.

Materials which can be suitably used for the protective collar are Mylar (polyester), polyethylene, polyurethane, polyvinyl chloride, polyimide, polytetrafluoroethylene, silicone and other materials which protect the cuff from metallic degradation and the edge of a metallic laser resistant layer. The protective collar can be relatively thin and may have a thickness of from about 5 to about 250 microns. Provided in the form of a tape, the tape may have a thin film of a conventional adhesive, such as a high-tack acrylic adhesive, in order to attach the protective collar to the tube 10. One acceptable material is a Mylar tape available from Minnesota Mining Manufacturing Co. The protective collar can also be applied by other known techniques, for example, as a liquid that is sprayed, dipped or brushed on and permitted to dry.

To provide laser protection for the tube, the tube has a laser resistant layer 19 which is indicated in FIG. 1(c). The laser resistant layer has a non-matte, reflective surface and a plurality of surface irregularities which are spaced from one another in a plurality of directions. For instance, as illustrated in the drawings, the surface irregularities can be spaced from one another along the length and circumference of the tube. The spacing between the center point of adjacent surface irregularities is selected so as to be smaller than the diameter of the laser spot so that when the laser impacts the laser resistant layer, the laser is incident on at least one surface irregularity. For instance, if a laser spot of 0.1 to 3 millimeters is used, the spacing between the center point of adjacent irregularities shown in FIG. 2 by "a" and "b", is typically within the range of from about 0.10 to about 3.0 millimeters, preferably from about 0.5 to about 1.5 millimeters and most preferably from about 0.75 to about 1.25 millimeters. It is to be understood that the surface irregularities of the present invention do not encompass a corrugated material which can cause line reflection of laser energy or be subjected to flattening when the material is flexed thereby resulting in a non-scattering reflective surface.

The laser resistant layer is a reflective material which also has sufficient flexibility so that it may be wrapped around tube 10 and when covered with an atraumatic layer be flexed during insertion and use without compromising laser protection and without forming sharp edges which might injure the patient. Suitable materials are metallic foils including metallic alloy foils, notably aluminum, silver, copper, tin and nickel with the preferred materials being copper, aluminum and silver. The metallic material can have a thickness of from about 10 to about 750 microns, preferably from about 15 to about 250 microns as measured by dial calipers after the surface irregularities are formed.

The size of the surface irregularities can be varied as long as it serves to sufficiently scatter the laser energy. Typically, the surface irregularities can have an average diameter of from about 0.10 to about 3.0 millimeters, preferably from about 0.25 to about 1.5 millimeters.

The surface irregularities can be a plurality of protrusions or depressions. The surface irregularities can have an average height or depth of from about 25 to about 500 microns that ca be achieved by passing metallic foil between a pair of calendaring rolls at least one of which has a surface which will impact the desired pattern of surface irregularities to the metallic foil. Other techniques for achieving a plurality of laser scattering surface irregularities without the occurrence of pinholes or other defects which might compromise laser protection may also be employed. It is to be understood that while the drawings illustrate the surface irregularities in a uniform diamond arrangement, the surface irregularities do not have to be the same size, height or depth and do not have to be uniformly arranged provided that the laser resistant layer has the capability of reflectively scattering laser energy.

The laser resistant layer can be wrapped around the tube as a single sheet and adhesively attached in a small area of overlap or as a series of concentric rings which partially overlap. However, it is preferred that the laser resistant layer be applied in the form of a spirally wrapped tape which partially overlaps the previous spiral without gaps or tears in the manner illustrated in FIG. 1(c) to provide effective laser resistance for the tube while maintaining a significant degree of flexibility. When spiral wrapping is used, the surface irregularities need not be present in the portion of the tape that is covered by a subsequent section of the tape.

The tape preferably contains adhesive on only one face and on only a part of the width of the tape. More specifically, as illustrated in FIG. 2, the tape can have a width "c" which is selected depending upon the particular size of the tube. For instance, the width of the tape can be from about 3 to about 26 millimeters, preferably from about 6 to about 13 millimeters. The position of the adhesive on the tape is selected so that it is convenient to spirally wrap the tape around the tube and so that in the overlapping portions, the adhesive substantially avoids contact with the previously wrapped tape. In this manner, the tape is adequately adhered to the tube, but when the tube is flexed to a reasonable degree, the overlapping portions of the tape are free to slide in compression or extension thereby maintaining flexibility and laser protection while reducing the possibility of kinking or the formation of sharp edges when covered with an atraumatic layer.

In one embodiment illustrated in FIG. 2, the adhesive extends from one edge to a point indicated by "d" and the overlap is achieved so that the adhesive portion does not contact the previously wrapped section of tape. It is to be understood that the adhesive need not extend to one edge of the tape or be present in the same location or be in the same amount on all sections of the tape as long as it adequately adheres the tape to the tube and provides the noted flexibility. For instance, when a spirally wrapped tape is used, some sections of the tape may not have any adhesive, but the spiral relationship provides adequate adherence of the tape to the tube thereby avoiding potential unraveling of the tape.

To achieve the foregoing objectives, the adhesive is present on an average of from about 1 to about 95% of the tape width, preferably from about 25 to about 35% of the tape width. Particularly effective results are obtained when the adhesive is applied from one edge to approximately one-third of the width of the tape and an overlap of one-half of the previous layer is used.

To provide laser protection immediately adjacent to the cuff, a laser resistant collar 20 is wrapped over the protective collar 18 and over a portion of the laser resistant layer 20 as illustrated in FIG. 1(d). The laser resistant collar is typically a metallic material including metallic alloys, such as tin, nickel, aluminum, silver and copper, with the collar preferably being copper foil, which is attached to the tube with a adhesive. To permit wrapping of the metallic material, it is preferably sufficiently thin to be flexible and typically has a thickness of from about 10 to about 250 microns. The laser resistant collar is preferably applied as an adhesive backed metallic foil having a width of from about 5 to about 50 millimeters and can be a piece of the laser resistant tape with surface irregularities as described above.

Since the protective collar 18 is immediately adjacent to cuff 15 and serves to protect the cuff from metallic degradation, the laser resistant collar 20 can be placed in close proximity to the cuff so that the spacing between the cuff and the laser resistant collar indicated in FIG. 1(d) at 21 can be extremely small thereby providing additional laser protection. Although the edge of the laser resistant collar does not extend past the edge of the protective collar, the spacing 21 between the edge of the laser resistant collar and the cuff 15 is generally from about 0.01 to about 10 millimeters, preferably from about 0.1 to about 1 millimeters.

Covering the laser resistant collar 20 and at least a substantial portion of the laser resistant layer 19 from the proximal end of the cuff to the inflation tube 17 is an atraumatic layer. The atraumatic layer can be composed of any material that permits proper positioning of the endotracheal tube without trauma to the patient and can be sacrificed substantially without residual material and without creating an adverse medical condition when impacted by laser energy. For example, the atraumatic layer can be composed of a hydroxylated polyvinyl acetal sponge as described in U.S. Pat. No. 4,098,728 or a hydrogel or certain fire retardant fabrics described in U.S. Pat. No. 5,103,816, the contents of both of which are incorporated by reference.

In a more preferred embodiment illustrated in FIG. 1(e), the atraumatic layer is a low-linting, elastic, absorbent, thin textile material 22 which also provides cut resistance from sharp edges which might damage laser resistant layer 19. The textile material can be a woven, braided or knitted material which is impregnated with water or an aqueous solution to help keep the tube cool. That is, if the textile material is impacted with laser energy, the woven, braided or knitted nature of the material would tend to help transfer liquid to the site by an equilibrium phenomenon. The textile material may itself be hydrophobic or hydrophilic and can be natural or synthetic. If the laser energy exceeds the cooling effect caused by the wicking phenomenon of the textile material, the textile material is readily and cleanly sacrificed substantially without the occurrence of adverse byproducts whereupon the laser energy will impact the underlying laser resistant layer 19.

Cut resistant textile materials which can be used in the present invention are woven, braided or knitted materials which can be composed of various materials, such as polyester, nylon, cotton, linen, silk, and mixtures thereof. The cut resistant textile material has a thickness of from about 0.07 to about 1.6 millimeters, preferably from about 0.25 to about 0.75 millimeter. One especially acceptable textile material is a polyester knit material available from Liberty Industries Inc. which is designated "Miracle Wipes", catalog number 802-1003. The layer can be applied over the tube in any configuration, but would preferably be applied either as a continuous cylinder or as a flat sheet of material with a small overlap that is adhered in place. Other layers can also be present as long as they do not substantially adversely affect the advantages of the present invention.

The adhesive used to attach the atraumatic layer, as well as the laser resistant collar, laser resistant layer and protective collar can be the same or different and can be any conventional adhesive known in the art. Such adhesives are generally biocompatible, substantially non-degradable by moisture and are cleanly sacrificed when subjected to laser energy. For example, the adhesive can be a high tack acrylic adhesive that is commercially available from Minnesota Mining and Manufacturing Co.

Since the cut resistant textile layer can be cleanly sacrificed upon sustained laser impact, the layer can contain identification marks 23 and/or instructional (e.g., locational) markings 24. Although such markings can increase laser absorbance, it does not significantly degrade laser protection of the tube since the textile layer is not designed for primary laser resistance and can be sacrificed substantially without adverse consequences.

In one particular illustrative example, a red rubber endotracheal tube as shown in FIG. 1e having an inner diameter of approximately 6 millimeters and an outer diameter of approximately 10.6 millimeters extends approximately 31 centimeters from the proximal end to the distal end. The tube has an arcuate shape, a bevelled distal tip and a Murphy eye. The tube is provided with a latex cuff attached at both its distal and proximal ends and covered with latex. The distal end of the cuff is spaced approximately 2 centimeters from the distal end of the tube with the proximal end of the cuff extending to a point approximately 5 centimeters from the distal end of the tube. The cuff is inflated with a inflation tube that is incorporated into the wall of the endotracheal tube and is connected to a bubble chamber and has a connector for connection to a source of pressurized fluid. The endotracheal tube is provided at its proximal end with a 15 millimeter connector for connection to a ventilating device. Adjacent to the proximal end of the cuff is a protective collar which is a piece of Mylar 850 tape obtained from Minnesota Mining Manufacturing Co. which is approximately 2.5 centimeters in width and about 50 microns in thickness and which contains a high tack adhesive.

To provide laser protection, copper tape having a width of about 1.0 centimeter and a thickness of about 150 microns is spirally wrapped over the protective collar to a point where the inflation tube enters into the wall of the endotracheal tube. The copper foil has a plurality of surface depressions having center points that are arranged in diamond configuration and a depth of about 100 microns which are spaced approximately 1.0 millimeter. The surface depressions are obtained by passing the foil between calendaring rolls having corresponding protrusions. The tape is provided with an adhesive about 70 microns thick which extends from one edge to a point one-third of the width of the tape and the tape is wrapped so as to have a one-half width overlap so that there is a substantial absence of adhesive contact with previously wrapped tape.

An adhesive backed copper foil approximately 1.0 centimeter in width is wrapped over the protective collar adjacent the proximal end of the inflatable cuff so that it overlaps a portion of the spirally wrapped tape. A sheet of woven polyester material approximately 22 centimeter in length and approximately 3.3 centimeter in width is used to overwrap the tube between the proximal end of the cuff and the entry portion of the inflation tube with the overlapped portions of the textile layer being adhered together with a high tack, pressure sensitive adhesive available from Illbruck Corp. of Minneapolis, Minn. The textile layer contains identification markings and markings noting the distance of various points on the tube from the distal tip to facilitate placement of the tube in a patient.

In use the laser resistant endotracheal tube is contacted with sterile water or a sterile saline solution so as to impregnate the cut resistant textile layer. The tube is properly located in the patient using the locational markings on the textile layer and the tube is connected to a conventional ventilating device. The inflation tube is connected to a source of saline and the cuff is inflated to the minimum pressure required to make a tracheal seal and the cuff is typically packed with saturated pledgets to provide limited laser protection. Thereafter, the patient can be treated with laser radiation using known and tested lasers, such as carbon dioxide lasers, argon lasers, neodymium-yttrium-aluminum-garnet lasers or potassium-titanylphosphate lasers, to within recommended power density limits.

In another aspect of the present invention, the laser resistant tape can itself be employed to provide laser protection for tubing or other articles which may be in the general vicinity of laser surgery. For instance, tubing, wires or cables connecting the ventilating device to the connector of the endotracheal tube or electrical wire can be wrapped with the laser resistant tape to impart laser protection thereto. Additionally, reflective surfaces in areas in relatively close proximity to areas where lasers are to be used can be coated with the tape so that upon incidental contact with laser energy, scattered reflection will occur thereby reducing potential injury or damage by reflective laser energy. Of course, depending on the particular utility, the dimensions of the tape can be varied with illustrative widths being from about 3 to about 300 millimeters.

As a further aspect of the present invention, laser protection for patients or pieces of equipment or general areas can be achieved by covering them with a laser resistant material which contains a laser resistant layer having the previously described surface irregularities. For instance, a sheet of laser resistant material 30, as illustrated in FIG. 3, can be comprised of a laser resistant layer 31 which contains a plurality of surface irregularities which are spaced from one another in a plurality of directions in the manner discussed previously. In this respect, however, if the material is constructed so that either face can be potentially exposed to laser energy, then both faces of the laser resistant layer must have the plurality of surface irregularities thereon.

The laser resistant layer can be laminated to another layer 32 which provides certain comfort or other functional properties. For instance, the layer can be a cut resistant textile layer having the characteristics noted above. The layer 32 can have identification markings 33 or instructional information (not shown) marked thereon. If cut resistance is not a concern, layer 32 can be constructed of other materials such as the hydroxylated polyvinyl acetal sponge described in aforementioned U.S. Pat. No. 4,098,728 or the hydrogel or fire retardant fabric described in aforementioned U.S. Pat. No. 5,103,816.

The laser resistant material may also have other layers for comfort, warmth or other reasons. For example, an additional layer 34 can be used to form a laminate with the laser resistant layer therebetween. The additional layer may be the same or different from layer 32. For instance, if the laser resistant material is to be used as a surgical drape or individual-contacting, protective material and only one side of the material is designed for potential laser exposure, the other side may contain a layer of cushioning material, such as a quilted textile, that will provide comfort to the individual. Still further layers on either side of the laser resistant layer including additional laser resistant layers may also be present.

Although the laser resistant material has been illustrated in rectilinear form, it can be constructed of any suitable shape depending on its particular utility. As noted above, the laser resistant material can be formed into a surgical drape which is sized and shaped for the particular area where laser surgery is to be performed. Other illustrative utilities for the material are as a protective cover for equipment that is to be used in the vicinity where lasers are to be used, or as various pieces of apparel for the patient or personnel who are working in the vicinity where lasers are operating. In this last respect, the laser resistant material can be fashioned into an eye shield that can be placed over the eyes of a patient during laser surgery.

A still further aspect of the present invention relates to a laser resistant article comprising an article and a laser resistant layer at least partly covering the article. The laser resistant layer is comprised of a plurality of sections of a laser resistant material with at least some of the sections having portions that contact and are adhered to the article and other portions which overlap other sections of the laser resistant material and are free to move in the portions of overlap so that upon reasonable flexing of the article structural attrition and loss of laser protection is substantially avoided.

The article can be tubing, wires, cables, or any other article wherein laser protection is advantageous while maintaining flexibility. The laser resistant layer is comprised of a laser absorbing or reflective material and is preferably a laser reflective metallic foil selected from copper, aluminum, silver, tin, nickel and metal alloys. The metallic foil can be flat, corrugated or, preferably, contains a plurality of surface irregularities which are spaced from one another in a plurality of directions and which reflectively scatter laser energy in the manner described previously.

The laser resistant layer has a plurality of sections which are directly or indirectly adhered through one or more optional layers to the article. At least some of the sections have portions which overlap other sections of the laser resistant layer. This arrangement can be achieved by forming a plurality of overlapping concentric sections or by spirally wrapping the article with an elongated piece of the laser resistant material so that overlapping portions occur.

The laser resistant layer can be adhered to the article by using a conventional adhesive that is applied to the face of the laser resistant material that contacts the article or by applying the adhesive to the article and applying the laser resistant material thereon. If the adhesive is applied to the laser resistant material, the adhesive is present so that when the laser resistant material is attached to the article, the adhesive substantially avoids contact with previously applied sections of the laser resistant material. This can be achieved with a laser resistant tape that is described above If the adhesive is applied to the article first, the adhesive is not applied to the total surface to be covered by the laser resistant material since flexibility will be significantly impeded. Instead, the adhesive can be applied in a variety of configurations which effectively adheres the laser resistant material to the article substantially without sacrificing flexibility. For instance, if the laser resistant material is applied as a plurality of separate concentric sections, the adhesive can be likewise applied as a plurality of concentric portions which are from about 1 to about 95%, preferably from about 25 to about 35% of the width of the section of the laser resistant material. Similarly, if the laser resistant material is applied as a spiral wrapping, the adhesive can be present on the article in a corresponding spiral with the same width relationship. Other configurations of the laser resistant material and the adhesive which effectively permit attachment of the laser resistant material to the article while maintaining flexibility will be apparent to those of ordinary skill in the art and are within the scope of the invention.

The laser resistant article can further be provided with additional layers in the manner explained above. For instance, the article can be provided with one or more layers of hydrogel, fire retardant fabric, cut resistant textile material described above or other materials.

The various aspects of the invention provide substantial laser protection for the article or individual to be protected in a relatively convenient manner. The actual level of protection depends on the precise materials and laser energy employed. It is to be understood that the various aspects of the invention are not impervious to laser energy and that under substantial exposure to laser energy, the laser protection can be compromised.

While certain preferred features of the inventions have been shown by way of illustration and discussion, many modifications will occur to those of ordinary skill in the art. It is to be understood therefor that the following claims are intended to cover all such modifications and changes as fall within the spirit and scope of the invention.

We claim:

1. A laser resistant endotracheal tube comprising:
   a) a tube capable of providing gas to a patient, said tube having a distal end for insertion in the patient and a proximal end for connection with a respirating device; and
   b) a laser resistant layer surrounding the tube along at least a portion of the length of the tube between the distal end and the proximal end, said laser resistant layer comprising a non-corrugated, non-woven reflective metal foil material having a plurality of surface irregularities which are spaced from one another in a plurality of directions and which reflectively scatter laser energy.

2. The laser resistant endotracheal tube of claim 1 wherein the surface irregularities are depressions.

3. The laser resistant endotracheal tube of claim 2 wherein the depressions have a center point which is spaced from the center point of an adjacent depression in the range of from about 0.10 to about 3 millimeters.

4. The laser resistant endotracheal tube of claim 3 wherein the depressions have a center point which is spaced from the center point of an adjacent depression in the range of from about 0.5 to about 1.5 millimeters.

5. The laser resistant endotracheal tube of claim 1 wherein the laser resistant layer is provided as an overlapping spirally wrapped tape.

6. The laser resistant endotracheal tube of claim 5 wherein the tape contains an adhesive on only one face.

7. The laser resistant endotracheal tube of claim 6 wherein the adhesive on the one face of the tape is present on average of from about 1 to about 95% of the width of the tape and the tape is spirally wrapped s that in the overlapping portions, the adhesive substantially avoids contact with previously wrapped tape.

8. The laser resistant endotracheal tube of claim 7 wherein the adhesive on the one face of the tape is present on an average of from about 25 to about 35% of the width of the tape.

9. The laser resistant endotracheal tube of claim 7 wherein the tape has a width of from about 3 to about 26 millimeters.

10. The laser resistant endotracheal tube of claim 1 including an inflatable sealing cuff positioned adjacent the distal end of the tube.

11. The laser resistant endotracheal tube of claim 10 wherein the laser resistant layer is comprised of a metal selected from the group consisting of copper, aluminum, silver, tin and nickel.

12. The laser resistant endotracheal tube of claim 11 including a protective collar positioned adjacent the inflatable sealing cuff and between the tube and the laser resistant layer, said protective collar inhibiting damage to the inflatable sealing cuff by the metal laser resistant layer.

13. The laser resistant endotracheal tube of claim 12 wherein the protective collar extends from the proximal end of the inflatable sealing cuff toward the proximal end of the tube for from about 5 to about 50 millimeters.

14. The laser resistant endotracheal tube of claim 13 wherein the protective collar extends from the proximal end of the inflatable sealing cuff toward the proximal end of the tube for from about 20 to about 30 millimeters.

15. The laser resistant endotracheal tube of claim 12 wherein the protective collar has a thickness of from about 5 to about 250 microns.

16. The laser resistant endotracheal tube of claim 12 wherein the protective collar is composed of a material selected from polyester, polyethylene, polyurethane, polyvinyl chloride, polyimide, polytetrafluoroethylene and silicone.

17. The laser resistant endotracheal tube of claim 16 wherein the protective collar is polyester.

18. The laser resistant endotracheal tube of claim 1 wherein the tube is provided with an outer atraumatic layer that surrounds the laser resistant layer.

19. The laser resistant endotracheal tube of claim 18 wherein the outer atraumatic layer that surrounds the laser resistant layer is a textile layer that is knitted or woven or braided.

20. The laser resistant endotracheal tube of claim 19 wherein the textile layer has a thickness of from about 0.07 to about 1.6 millimeters.

21. The laser resistant endotracheal tube of claim 20 wherein the textile layer is selected from the group consisting of polyester, nylon, cotton, linen, silk and mixtures thereof.

22. The laser resistant endotracheal tube of claim 21 wherein the textile layer is knitted polyester.

23. The laser resistant endotracheal tube of claim 18 wherein the textile layer contains identification or instructional markings.

24. The laser resistant endotracheal tube of claim 1 wherein the tube is constructed of a material selected from the group consisting of red rubber, silicone, polyvinyl chloride, and latex.

25. The laser resistant endotracheal tube of claim 24 wherein the tube is constructed of red rubber.

* * * * *